(12) United States Patent
Kumar et al.

(10) Patent No.: US 8,630,710 B2
(45) Date of Patent: Jan. 14, 2014

(54) IMPLANTED CARDIAC DEVICE FOR DEFIBRILLATION

(75) Inventors: Uday N. Kumar, San Francisco, CA (US); John Warren White, San Francisco, CA (US); Joseph Allen Knight, Palm Harbor, FL (US); Kit Yee Au-Yeung, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 818 days.

(21) Appl. No.: 12/281,260

(22) PCT Filed: Mar. 1, 2007

(86) PCT No.: PCT/US2007/005515
§ 371 (c)(1),
(2), (4) Date: Nov. 25, 2008

(87) PCT Pub. No.: WO2007/103262
PCT Pub. Date: Sep. 13, 2007

(65) Prior Publication Data
US 2009/0149902 A1 Jun. 11, 2009

Related U.S. Application Data

(60) Provisional application No. 60/778,118, filed on Mar. 1, 2006.

(51) Int. Cl.
*A61N 1/00* (2006.01)
(52) U.S. Cl.
USPC .......................................................... 607/36
(58) Field of Classification Search
USPC .......................................................... 607/36
See application file for complete search history.

(56) References Cited

U.S. PATENT DOCUMENTS

| | | | |
|---|---|---|---|
| 3,835,864 A | * | 9/1974 | Rasor et al. ..................... 607/36 |
| 4,180,078 A | | 12/1979 | Anderson |
| 5,163,427 A | | 11/1992 | Keimel |
| 5,193,535 A | | 3/1993 | Bardy et al. |

(Continued)

OTHER PUBLICATIONS

Mehra et al.: Where are we, and where are we heading in the device management of ventricular tachycardia/ventricular fibrillation?; Heart Rhythm; vol. 4; No. 1; pp. 99-103; Jan. 2007.

(Continued)

*Primary Examiner* — Christopher D Koharski
*Assistant Examiner* — Nadia Ahmad
(74) *Attorney, Agent, or Firm* — Shay Glenn LLP

(57) ABSTRACT

An implantable medical device for delivering electrical cardiac therapy includes a first implantable housing containing a battery. There is also a second implantable housing separate from the first implantable housing and containing at least one of: electronic circuitry adapted to evaluate and initiate electrical cardiac therapy, a storage capacitor and an electrode structure comprising a sensing electrode, a pacing electrode and a therapy electrode. The electronic circuit, the storage capacitor or the electrode structure are electrically connected to the battery. Alternatively, there is an implantable medical device for delivering electrical cardiac therapy having an implantable structure containing the following electrically connected components: a battery, electronic circuitry adapted to evaluate and initiate electrical cardiac therapy, a storage capacitor and an electrode structure comprising a sensing electrode, a pacing electrode and a therapy electrode. A method of providing electrical cardiac therapy is also provided.

11 Claims, 17 Drawing Sheets

(56) References Cited

U.S. PATENT DOCUMENTS

| | | | |
|---|---|---|---|
| 5,282,845 A | 2/1994 | Bush et al. | |
| 5,312,440 A * | 5/1994 | Hirschberg et al. | 607/5 |
| 5,314,451 A | 5/1994 | Mulier | |
| 5,331,966 A | 7/1994 | Bennett et al. | |
| 5,433,730 A | 7/1995 | Alt | |
| 5,470,345 A | 11/1995 | Hassler et al. | |
| 5,827,326 A * | 10/1998 | Kroll et al. | 607/5 |
| 5,991,656 A | 11/1999 | Olson et al. | |
| 6,246,908 B1 | 6/2001 | Chattipakorn et al. | |
| 6,275,729 B1 | 8/2001 | O'Phelan et al. | |
| 6,633,780 B1 | 10/2003 | Berger | |
| 7,069,075 B2 * | 6/2006 | Olson | 607/5 |
| 7,174,207 B2 | 2/2007 | Dodd et al. | |
| 7,231,252 B2 * | 6/2007 | Duncan et al. | 607/36 |
| 7,734,343 B2 | 6/2010 | Ransbury et al. | |
| 7,899,537 B1 * | 3/2011 | Kroll et al. | 607/36 |
| 2002/0035380 A1 | 3/2002 | Rissmann et al. | |
| 2002/0082647 A1 | 6/2002 | Alferness et al. | |
| 2003/0045904 A1 | 3/2003 | Bardy et al. | |
| 2004/0034272 A1 | 2/2004 | Diaz et al. | |
| 2004/0068302 A1 | 4/2004 | Rodgers et al. | |
| 2004/0127952 A1 | 7/2004 | O'Phelan et al. | |
| 2004/0147961 A1 | 7/2004 | O'Phelan et al. | |
| 2005/0102014 A1 | 5/2005 | Lau et al. | |
| 2005/0131475 A1 | 6/2005 | Smits | |
| 2005/0182389 A1 | 8/2005 | LaPorte et al. | |
| 2006/0023400 A1 | 2/2006 | Sherwood | |
| 2006/0247688 A1 | 11/2006 | Olson et al. | |

OTHER PUBLICATIONS

Olson et al.: Onset and stability for ventricular tachyarrhythmia detection in an implantable pacemaker, cardioverter and defibrillator; Comput Cardiol; pp. 167-170; 1986.

* cited by examiner

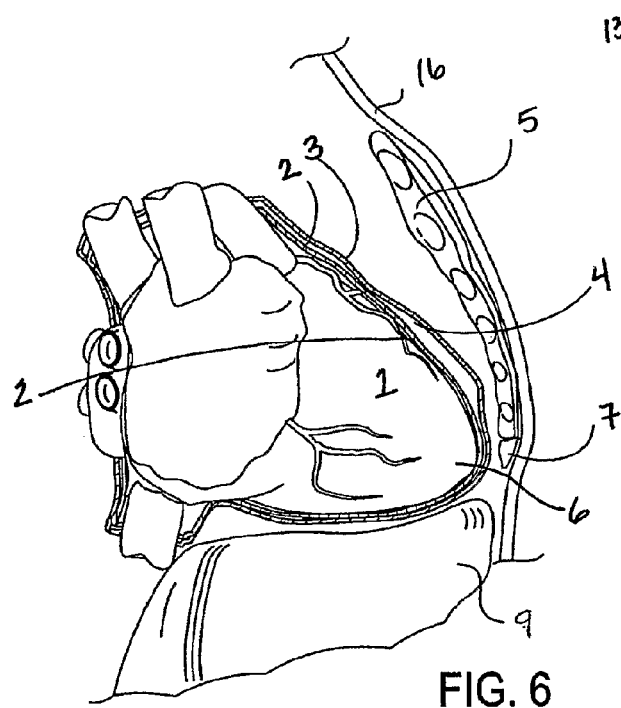
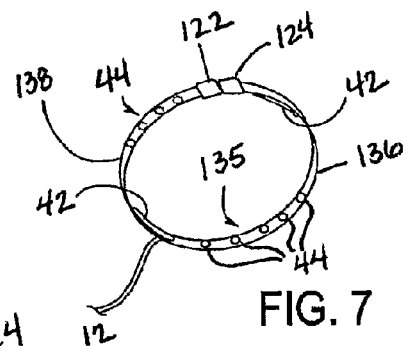
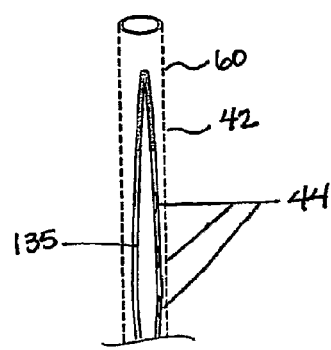
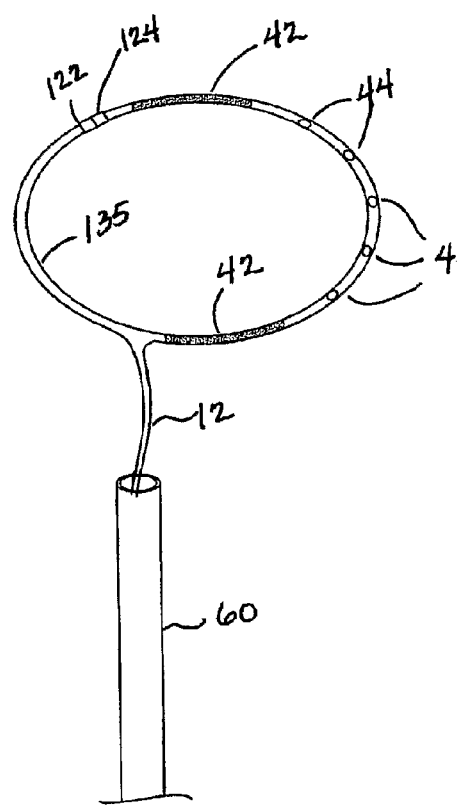
FIG. 6
FIG. 7
FIG. 8
FIG. 9

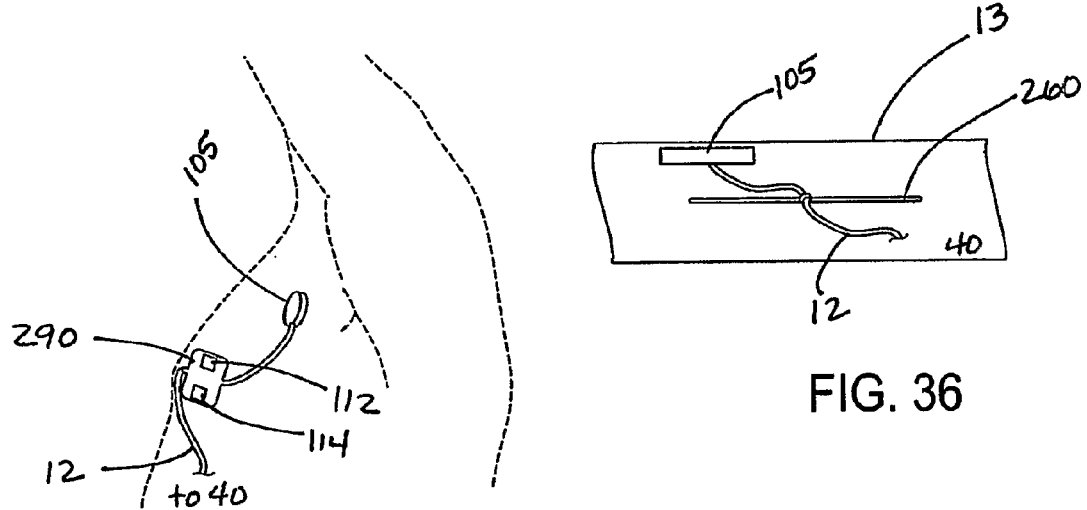
FIG. 35
FIG. 36
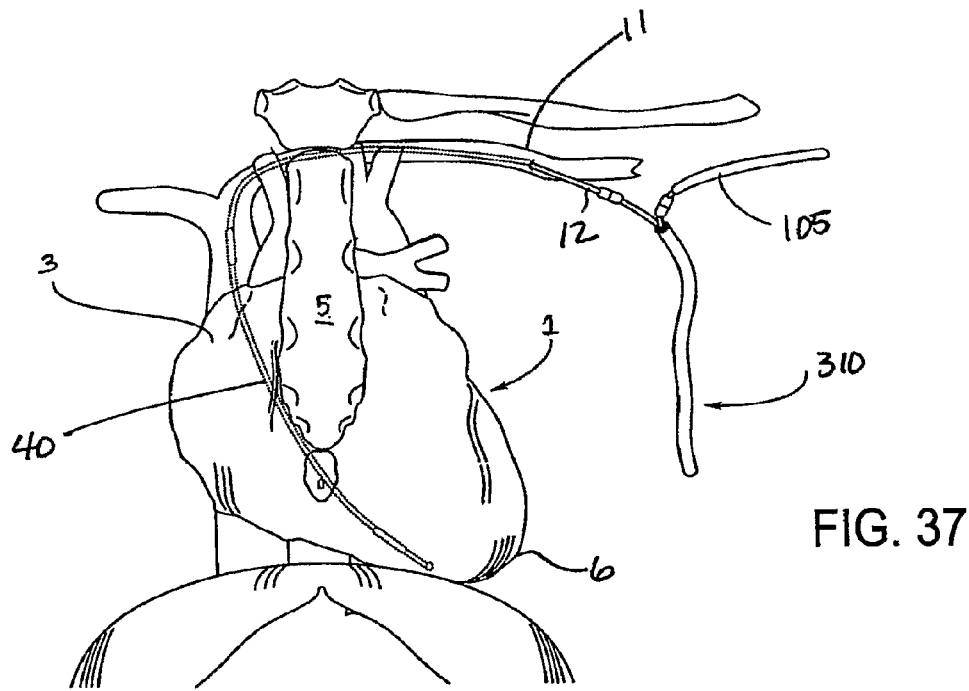
FIG. 37

IMPLANTED CARDIAC DEVICE FOR DEFIBRILLATION

CROSS REFERENCE TO RELATED APPLICATIONS

This application claims the benefit of PCT/US2007/005515 filed Mar. 1, 2007, which claims the benefit under 35 U.S.C. 119 of U.S. Patent Application No. 60/778,118 filed Mar. 1, 2006, titled "Implanted Cardiac Device for Defibrillation" to Kumar, et al., and which incorporated herein by reference in their entirety.

BACKGROUND OF THE INVENTION

FIG. 1 illustrates a conventional implantable cardioverter-defibrillator (ICD). An electrode structure 40 has been passed thought the subclavian vein 11 into the heart 1. Therapy electrodes 42 are used to deliver energy to shock the heart if and when abnormal cardiac activity is detected. Sensing and/or pacing electrodes 44 are used to monitor cardiac activity and/or pace the heart if necessary. The housing 10 contains the conventional components used to operate an ICD. A battery 10 is used to provide power to charge a capacitor 25 and operate electronic circuitry 15. Electronics circuitry 15 monitor and analyze the cardiac signals detected by the sensing and pacing electrodes 44. When an abnormal condition is detected by the electronic circuitry 15, the capacitor 25 discharges to the therapy electrodes 42 to apply a therapeutic shock to the heart 1. Thereafter, the battery 10 charges the capacitor 25 in preparation for the next shock.

One ongoing challenge is degrading battery performance over time and the eventual need for battery replacement. When the battery is replaced, the entire housing 10 including all ICD components is removed even though only the battery needs service. The capacitors and circuits are not in need of service replacement and are highly reliable components of the ICD system. One shortcoming of the prior art is that the use of a single housing for both permanent components like capacitors and electronic circuitry with non-permanent components like batteries leads to unnecessary removal of ICD components that could otherwise remain implanted and operational.

Additionally, therapy and sensing electrodes are placed to provide accurate detection of cardiac activity and allow for the delivery of therapy. Ideally, therapy electrodes would discharge primarily around or near the cardiac muscle tissue especially the ventricles. As illustrated in FIG. 1 however, the therapy vector created by the illustrated electrode placement results in more tissue than only cardiac tissue being subjected to the shock. The application of ICD shocks to surrounding tissue, nerves and muscle can be painful for patients.

There is a need therefore for improved ICD systems that address the various shortcomings of existing ICD systems and components.

SUMMARY OF THE INVENTION

In one embodiment of the present invention, there is provided an implantable medical device for delivering electrical cardiac therapy having a first implantable housing containing a battery and a second implantable housing separate from the first implantable housing. The second implantable housing contains at least one of: electronic circuitry adapted to evaluate and initiate electrical cardiac therapy, a storage capacitor and an electrode structure comprising a sensing electrode, a pacing electrode and a therapy electrode. The electronic circuit, the storage capacitor or the electrode structure is electrically connected to the battery. In one aspect, the second implantable housing contains at least two of: electronic circuitry adapted to evaluate and initiate electrical cardiac therapy; a storage capacitor and an electrode structure comprising a sensing electrode, a pacing electrode and a therapy electrode. In another aspect, the second implantable housing contains all of: an electronic circuitry adapted to evaluate and initiate electrical cardiac therapy; a storage capacitor and an electrode structure comprising a sensing electrode, a pacing electrode and a therapy electrode. In still another aspect, the second implantable housing is adapted for implantation within the vasculature. In another aspect, the second implantable housing is adapted for subcutaneous implantation. In still another aspect, the second implantable housing is adapted and configured to lie within the pericardial space and at least partially conform to the shape of the ventricular portion of the heart. In another aspect, the second implantable housing is a flexible band or an elongate, generally cylindrical body.

In another aspect, the second implantable housing also includes a guide lumen extending through the second housing. In another aspect, the second implantable housing is sufficiently long to encircle a portion of the ventricular portion of the heart. In another aspect, the second housing has a stowed condition for delivery to an implantation location and a deployed condition for operation in an implantation location. In another aspect, the second housing is adapted for delivery to an implantation location using a hollowed cannula while in the stowed condition. In one aspect, the stowed condition is rolled and deployed condition is unrolled or folded and unfolded. In another aspect, the stowed condition is uninflated and the deployed condition is inflated. In still another aspect, the deployed condition includes a first section adapted to conform to a portion of the posterior ventricular epicardial portion of the heart and a second section adapted to conform to a portion of the anterior ventricular epicardial portion of the heart. In another aspect, the first section is magnetically attached to the second section when the second housing is in a deployed condition.

In another embodiment, there is provided a method of providing electrical cardiac therapy by implanting a first housing containing a battery into a first implantation site within the body. Then, implanting a second housing separate from the first housing into a second implantation site within the body. The second housing contains at least one of: electronic circuitry adapted to evaluate and initiate electrical cardiac therapy; a storage capacitor and an electrode structure comprising a sensing electrode, a pacing electrode and a therapy electrode, wherein the electronic circuit, the storage capacitor or the electrode structure is electrically connected to the battery. In one aspect, the second implantation site is subcutaneous, within the vasculature, or within the pericardial space. In another aspect, the first implantation site is closer to the surface of the skin than the second implantation site. In yet another aspect, the second implantation site is accessed using a sub-xiphoid process approach. In one aspect, the electrode structure is in contact with the epicardium. In another aspect, the method includes forming a cavity within the body that is used as the second implantation site.

23. The method of providing electrical cardiac therapy according to claim 22 wherein the forming step is performed by the second housing. In another aspect, the forming step is performed by the second housing as the second housing moves from a stowed condition to a deployed condition. In another aspect, the step of using a hollowed cannula to access the second implantation site is performed before the step of implanting the second housing. In another aspect, there is the step of positioning a section of the second housing within the pericardial space to conform to a portion of the posterior ventricular epicardial portion of the heart. In another aspect, there is the step of positioning a section of the second housing within the pericardial space to conform to a portion of the anterior ventricular epicardial portion of the heart. In another aspect, the second housing is used to at least partially encircle a portion of the ventricular portion of the heart.

In another embodiment, there is provided an implantable medical device for delivering electrical cardiac therapy having an implantable structure containing the following electrically connected components: a battery, electronic circuitry adapted to evaluate and initiate electrical cardiac therapy, a storage capacitor and an electrode structure comprising a sensing electrode, a pacing electrode and a therapy electrode. The implantable structure is adapted and configured for implantation within the pericardial space. In one aspect, at least a portion of the implantable structure is in direct contact with the epicardium.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings which.

FIG. 6 illustrates the pericardial space;

FIG. 7 illustrates an isometric view of an embodiment of a second housing;

FIGS. 8 and 9 illustrate an embodiment of a second housing in a stowed and deployed condition;

FIGS. 35 and 36 illustrate implanted ICD components with the first housing being implanted in an easier to reach location that is closer to the skin than the second housing;

FIG. 37 illustrates first and second housing embodiments in the form of elongate cylinders adapted for subcutaneous implantation;

DETAILED DESCRIPTION OF THE INVENTION

According to Rahul Mehra, PhD and Paul DeGroot, M S, in an article entitled, "Where are we, and where are we heading in the device management of ventricular tachycardia/ventricular fibrillation?" there are several challenges for increasing the acceptance of ICD therapy. Among the challenges is to improve the technology, facilitating implant and follow up from the physician's perspective and lowering morbidity from the patient's perspective. The same article points out that patients want ICDs that are smaller, result in fewer shocks, have less pain associated with defibrillation, require minimal follow-up, and last a long time so that the devices to not require replacement (Heart Rhythm, Volume 4, No. 1, January 2007). As will become clear in the detailed description that follows, embodiments of the ICD system and components of the present invention address these challenges and patient desires.

Figure 1:
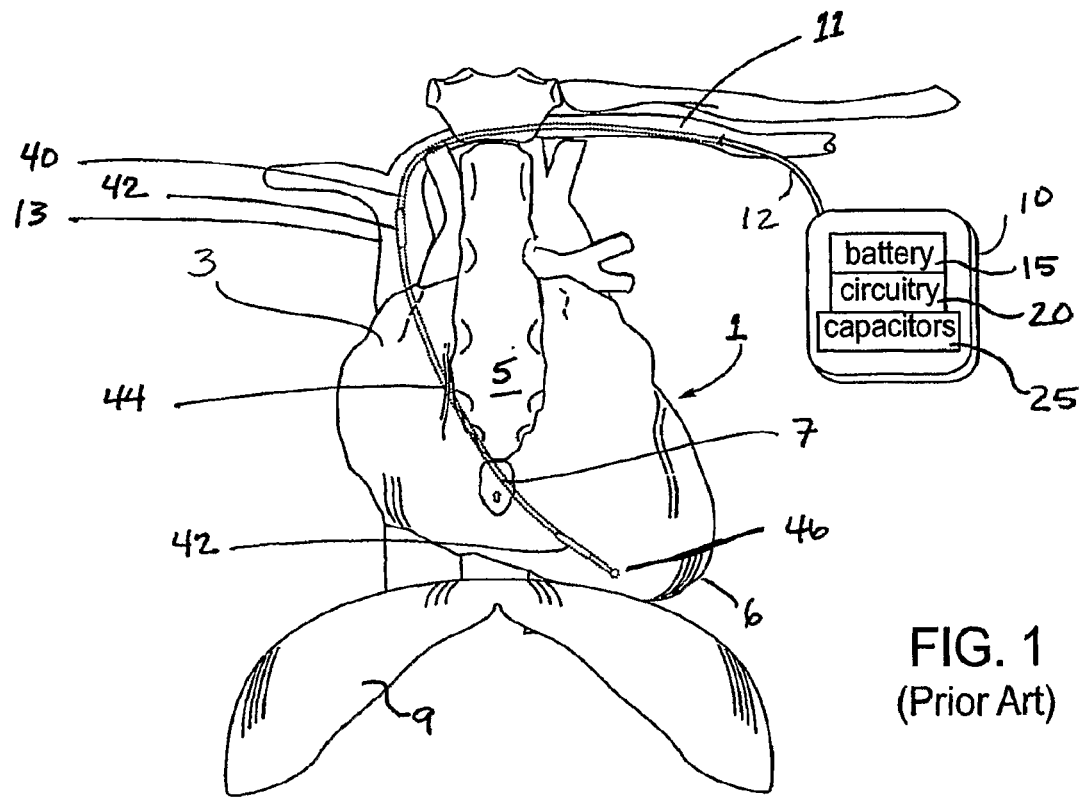
FIG. 1 illustrates conventional ICD components implanted within a body.
Figure 2:
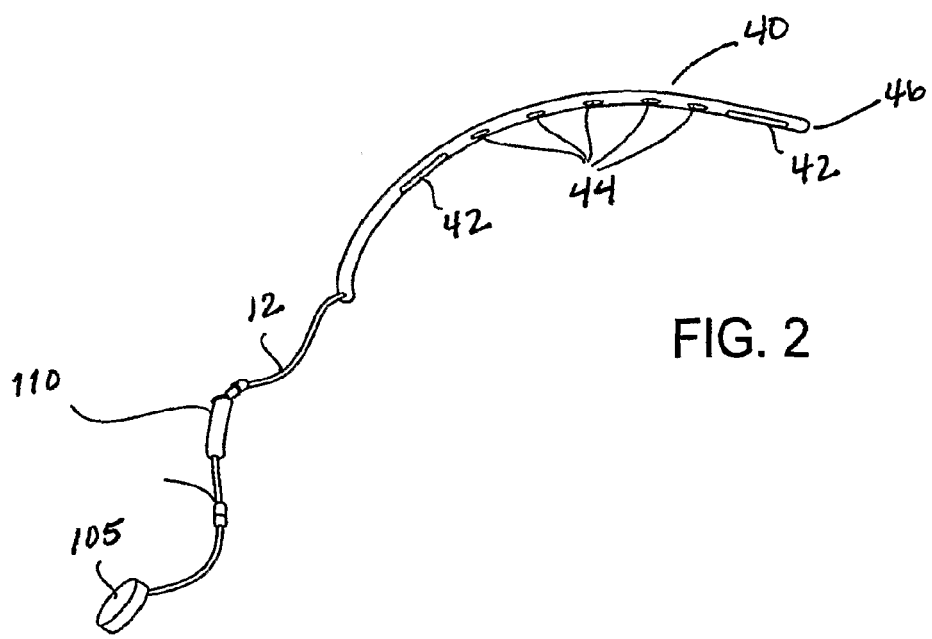
FIG. 2 illustrates one embodiment of the invention with a first housing, a second housing and a conventional electrode structure.

FIG. 2 illustrates an implantable medical device for delivering electrical cardiac therapy. A first implantable housing 105 contains a battery. A second implantable housing 110 is separate from the first implantable housing 105 and connected using a suitable biocompatible electrical connector 12. The second implantable housing may have any of a wide variety of shapes to provide maximum flexibility for component placement and implantation. The non-battery housing may be formed from any of a wide variety of biocompatible materials suited for implantation into the body. The second implantable housing 110 contains at least one of: electronic circuitry adapted to evaluate and initiate electrical cardiac therapy, a storage capacitor and an electrode structure comprising a sensing electrode, a pacing electrode and a therapy electrode. The electronic circuit, the storage capacitor or the electrode structure within the second housing 110 is electrically connected to the battery within housing 105. The components within the second housing are also connected to a conventional electrode structure having a sensing electrode 44, a pacing electrode 44 and at least one therapy electrode 42. While two therapy electrodes are illustrated in this exemplary embodiment, it is to be appreciated that the first housing 105 could be formed from suitable materials so that it may be used as another electrode as is conventional in the ICD arts.

Figure 3:
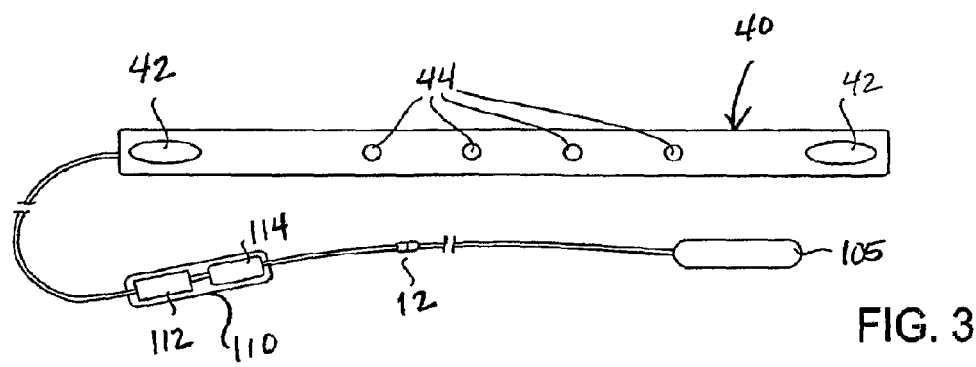
FIG. 3 illustrates another embodiment of the invention with a first housing, a second housing and a conventional electrode structure.

In the illustrated embodiment of FIG. 2 and as better seen in FIG. 3, the second housing 110 contains two ICD components, namely, electronic circuitry 112 adapted to evaluate and initiate electrical cardiac therapy and a storage capacitor 114. Since the ICD components are separated out from the battery in the first housing 105, the second housing 110 and the electrode structure 40 may be implanted into different areas. The implantation sites for these components may be selected from a broader list of potential implant sites since these components will not be disturbed when the battery in the first housing 105 is replaced. As will be detailed below, this allows the battery housing to be implanted into an implantation site that is easy to access in order to simplify the battery replacement process.

Figure 4:
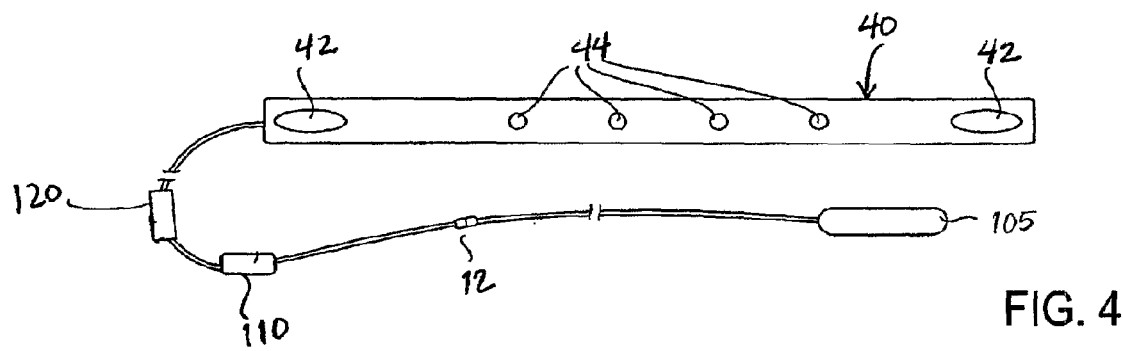
FIG. 4 illustrates another embodiment of the invention with a first housing, a second housing, a third housing and a conventional electrode structure.
Figure 5:
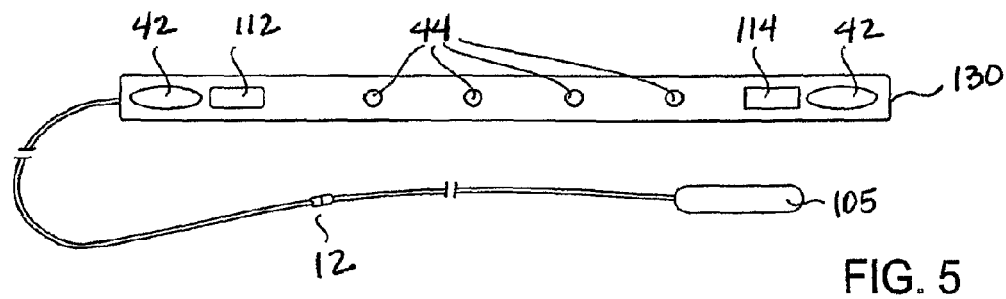
FIG. 5 illustrates another embodiment of the invention with a first housing and a second housing.

The non-battery components may be configured into a number of different configurations to provide greater flexibility in implantation and component placement. FIG. 4 illustrates an embodiment where the second housing 110 contains the electronic circuitry adapted to evaluate and initiate electrical cardiac therapy 112 while a third implantable housing 120 includes a capacitor 114. FIG. 5 illustrates an embodiment of a second housing 130 contains all of: an electronic circuitry 112 adapted to evaluate and initiate electrical cardiac therapy, a storage capacitor 114 and an electrode structure comprising a sensing electrode 44, a pacing electrode 44 and a therapy electrode 42. In this embodiment, the second housing 130 is a flexible band with components mounted thereon, affixed thereto or encapsulated within.

FIG. 6 illustrates a perspective view of the heart 1. The pericardium 2 surrounds the epicardium 3. The pericardial space 4 exists between the pericardium 2 and the epicardium 3. ICD component placement here has previously been limited to only the electrode structure and in that case only provided during invasive surgical procedures. The inventive ICD component configurations of the present invention enable improved utilization of the pericardial space. The pericardial space provides a number of advantages. Electrodes placed there are in direct contact for sensing and pacing. Importantly, therapy electrodes placed in the pericardial space are in direct contact with the epicardium creating a more efficient therapy vector since only the heart tissue lies in between. Patient pain during shocking is thus greatly reduced if not eliminated since there is no extraneous muscle, skin or other tissue within the shock vector when the therapy electrodes are on the heart. Placement in the pericardium enables direct placement of components on the ventricle to produce an optimal vector for therapy delivery resulting is less painful shocks. Moreover, placement of therapy electrodes in direct contact with the epicardium may require less power to be needed for therapy as compared to subcutaneous systems.

Embodiments of the ICD components according to the present invention may be adapted and configured for implantation into the pericardial space. FIG. 7 illustrates a second housing 135 having two sections 136, 138 shaped, and of sufficient length to encircle a portion of the heart. In one embodiment, the first section 136 is adapted to conform to a portion of the posterior ventricular epicardial portion of the heart and the second section 138 is adapted to conform to a portion of the anterior ventricular epicardial portion of the heart. The housing 135 contains all or some of electronic circuitry adapted to evaluate and initiate electrical cardiac therapy, a storage capacitor and an electrode structure comprising a sensing electrode, a pacing electrode and a therapy electrode.

The distal ends of the sections 122, 124 are adapted to join when they come into contact. Any suitable method of attaching the first section 136 to the second section 138 may be used. The attachment means may be in the form of magnets, adhesives, mechanical joining devices or other conventional techniques to join the ends 122, 124 together to maintain the housing 135 in position about the heart. In one embodiment, the end 122 may be male and the end 124 female where they are configured to use any complementary engagement features to secure the ends or adjust the size of the circumference of the second housing 135. In another embodiment, there are magnets within the distal ends 122, 124.

Figure 10:
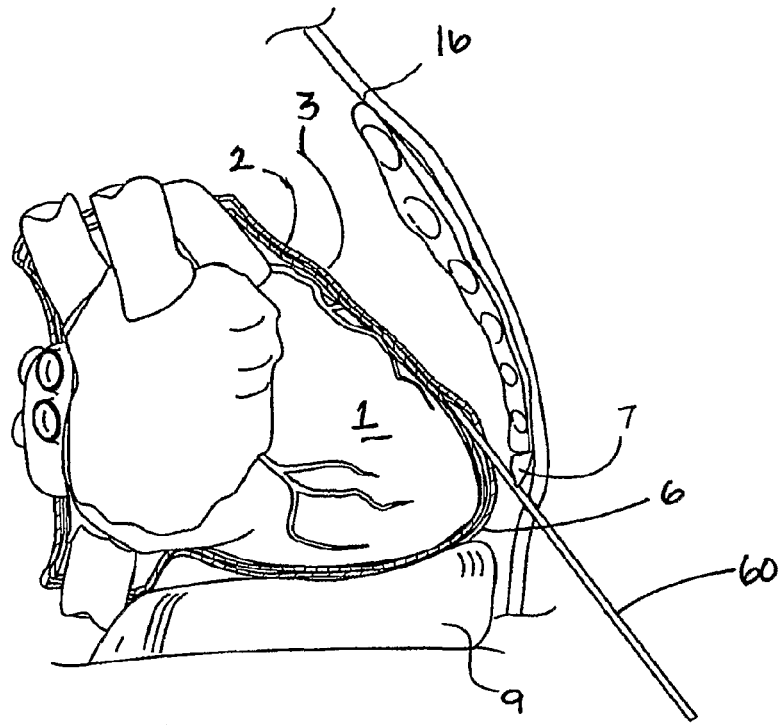
FIG. 10 illustrates a sub-xiphoid approach to the pericardial space.

The second housing 135 may be collapsed into a stowed condition to fit into a hollow cannula, a sheath or other suitable delivery device 60 as shown in FIG. 8. When released from the delivery device 60, the second housing 135 may be manipulated into the deployed, ready to use configuration illustrated in FIG. 9. Using a sub-xiphoid process approach as shown in FIG. 10, the delivery device 60 maneuvers the stowed housing 135 into position near the apex 6 of the heart. The housing 135 is released from the device 60. The housing 135 is advanced about the heart, the sections 136, 138 extend anteriorly and posteriorly. The sections 136 and 138 are manipulated about the anterior and posterior surfaces. Thereafter, when the ends 122, 124 are in proximity, the ends 122, 124 are joined together to define a loop about the epicardium in the desired cardiac therapy position.

Figure 11:
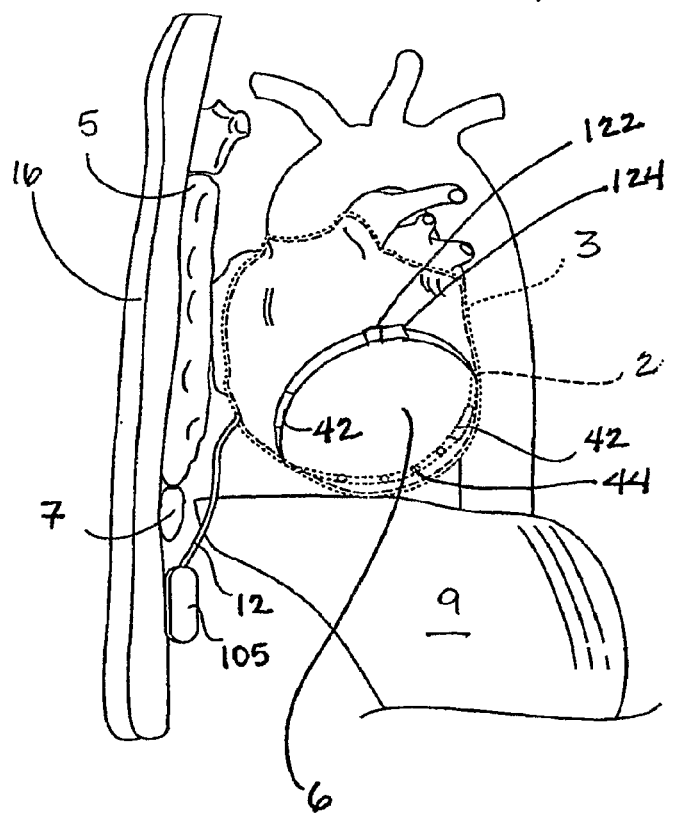
FIG. 11 illustrates the housing of FIG. 7 implanted into the pericardial space.

In the illustrative embodiment of FIG. 11, the ends 122, 124 are shown joined in the anterior portion of the heart. The ends 122, 124 could be could be joined in any of a wide variety of locations. The arms 136, 138 may be of the same length of different lengths. The lengths could be selected based upon implantation technique and the estimated or desired location where the ends 122, 124 will meet. The sections 136, 138 could be adapted so that the ends 122, 124 join in a lateral portion of the pericardial space, an anterior portion of the pericardial space, or a posterior portion of the pericardial space. FIG. 11 illustrates the embodiment of FIG. 7 implanted within the pericardial space with the ends meeting in the anterior portion of the pericardial space. The components within the second housing 135 are connected with connections 12 to the battery in the first housing 105. In one embodiment, the first section 136 is magnetically attached to the second section 138 when the second housing 135 is in a deployed condition. In one embodiment, there is provided a kit containing a number of housings 135 where the sections 136, 138 have various lengths. Different section lengths provide for different size hearts as well as different locations on the heart where the distal ends 122, 124 will join. In addition, the sections 136, 138 may have a predefined curve to comply with one or more portions of the contours of the heart.

While described above with regard to the housing 135, it is to be appreciated that the details, modifications and variations of the design of housing 135 may be applied other housing embodiments described herein.

Figure 12:
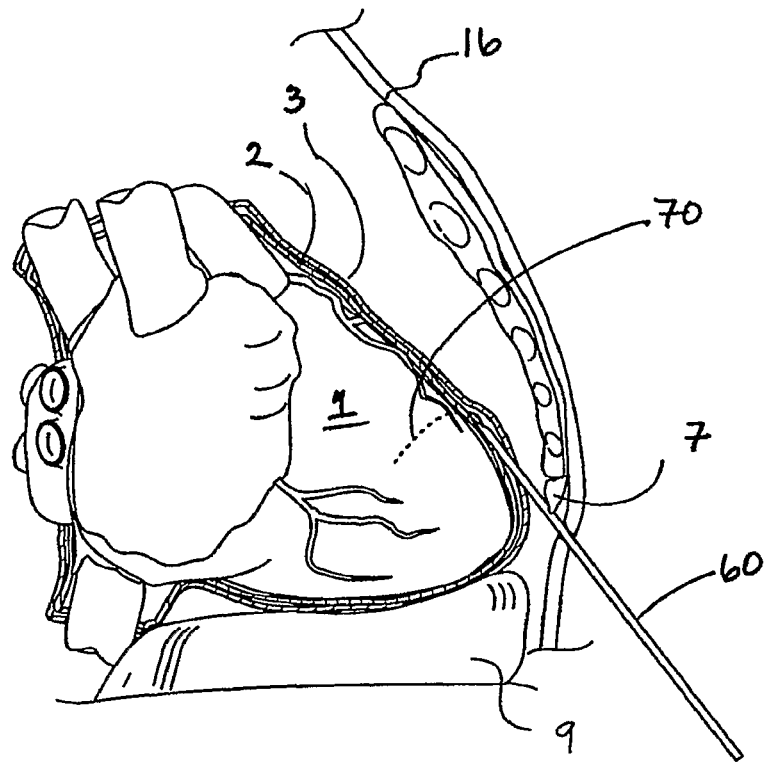
FIGS. 12-16 illustrate a method of using a guide wire to implant a housing within the pericardial space.
Figure 13:
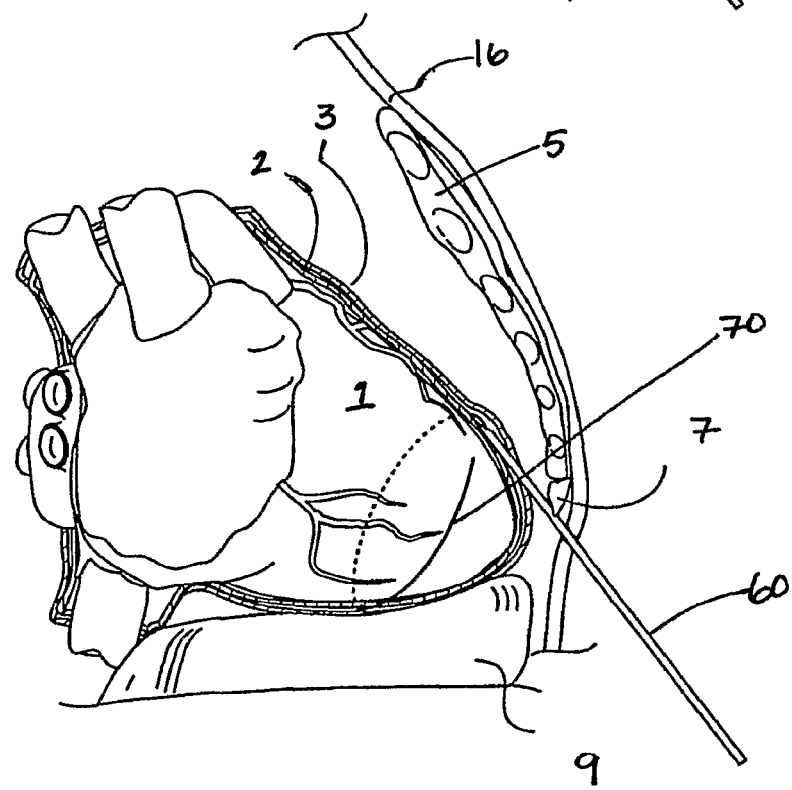
Figure 14:
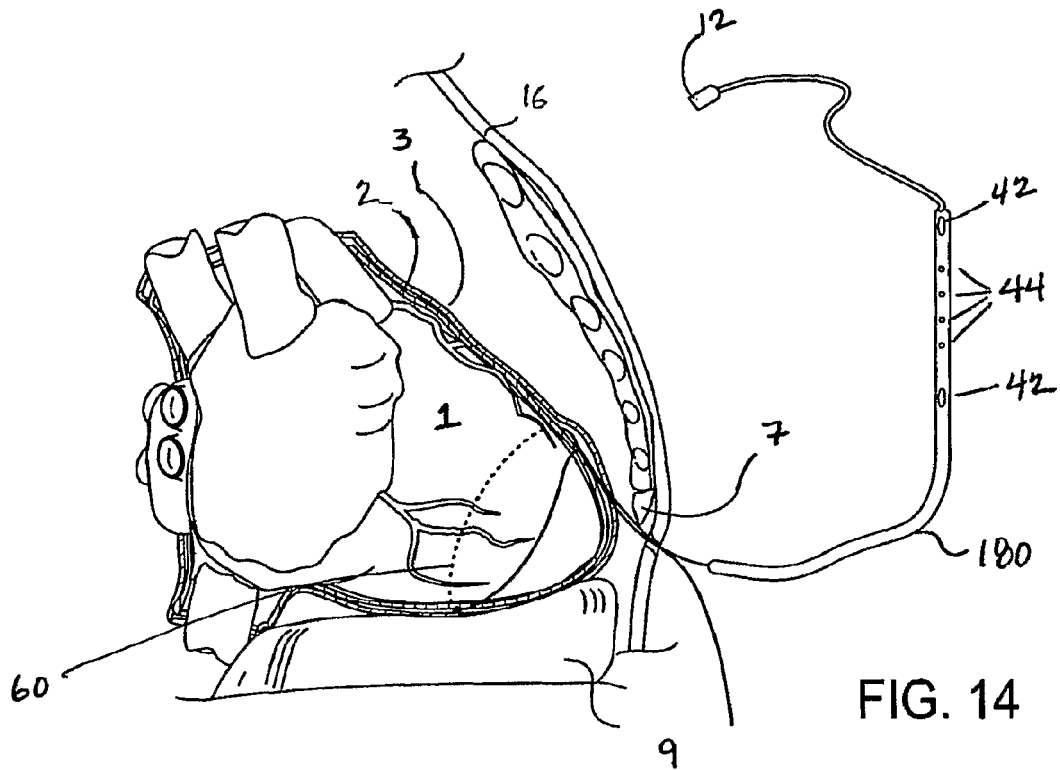
Figure 15:
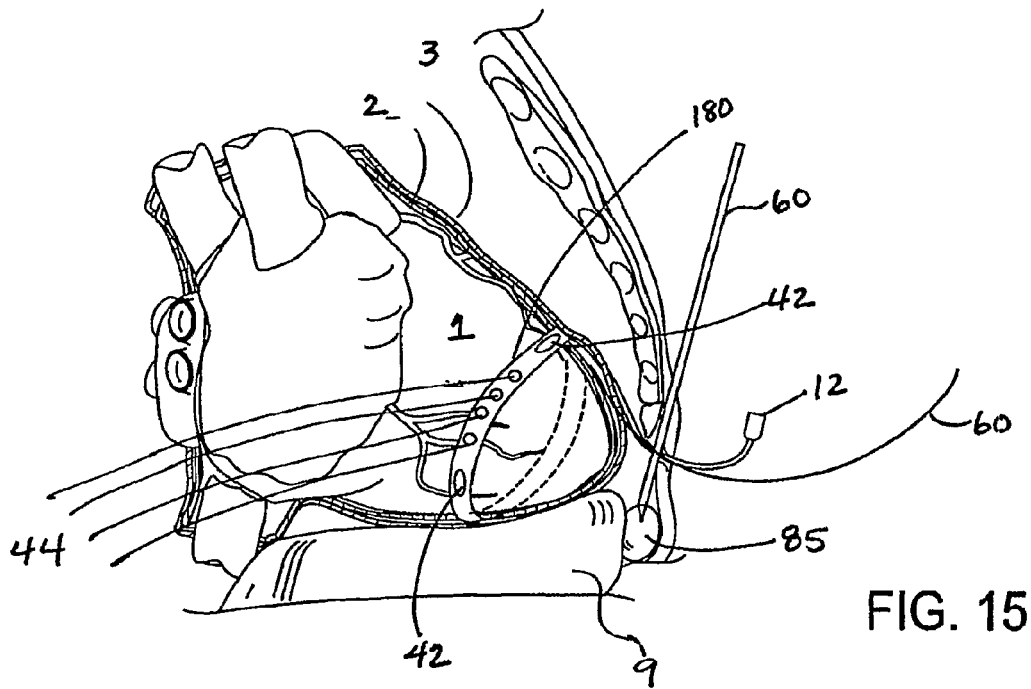
Figure 16:
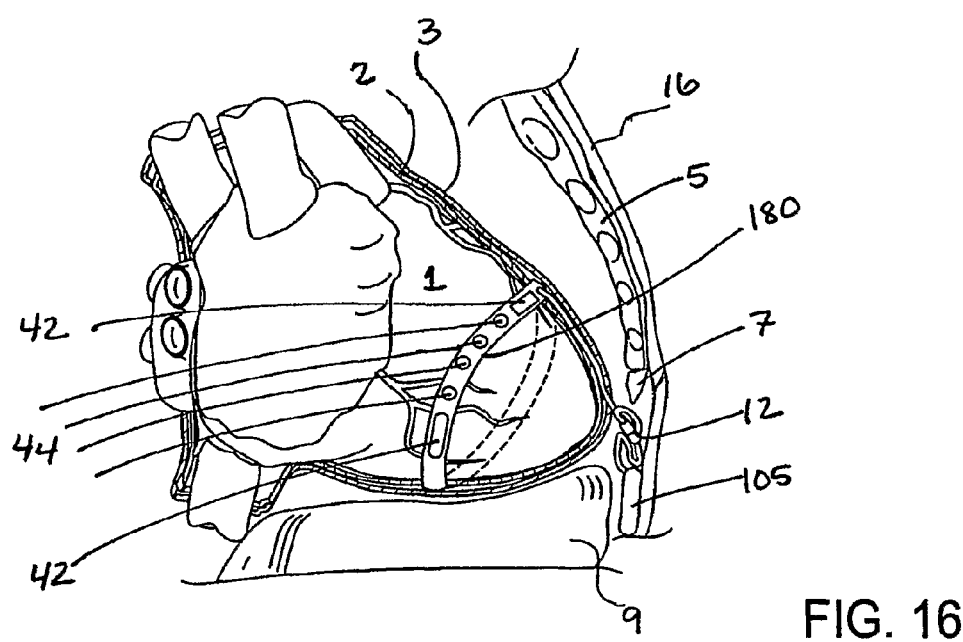

FIGS. 12-16 illustrate another housing embodiment according to the present invention. In this alternative embodiment, the second housing 180 is sufficiently long to encircle a portion of the ventricular portion of the heart. The housing 180 contains at least one of electronic circuitry adapted to evaluate and initiate electrical cardiac therapy, a storage capacitor and an electrode structure comprising a sensing electrode, a pacing electrode and a therapy electrode. The second implantable housing 180 is adapted and configured to lie within the pericardial space and at least partially conform to the shape of the ventricular portion of the heart. The components within the housing 180 are electrically connected to a battery within a first and separate housing 105 (see FIG. 16). One technique to implant the second housing 180 includes the use of a guide wire 60 as a lead line to thread the housing 180 within the pericardial space 4. First, as shown in FIG. 12, a guide wire 60 is introduced into the pericardial space 4 using an appropriate delivery tool 60 and, optionally, a sub-xiphoid process approach as illustrated. The guide wire 60 is advanced about the heart 1 in the pericardial space 4 as shown in FIG. 13. Next, as shown in FIG. 14, the housing 180 is attached to guide wire 60. The guide wire 60 is withdrawn from the pericardial space and pulls the housing into the space as illustrated in FIG. 15. As the end comes back around the section could be attached to itself at an appropriate location to secure the housing at the desired circumference for a selected implantation site within the pericardial space. FIG. 15 also shows a spacing being created in the subcutaneous space using a dissecting balloon 85. The spacing will be used to implant the first housing 105 as shown in FIG. 16. In FIG. 16, the second housing 180 has been electrically connected to the first housing 105 using connections 12 and the incision used to implant the housings is closed.

Figure 17:
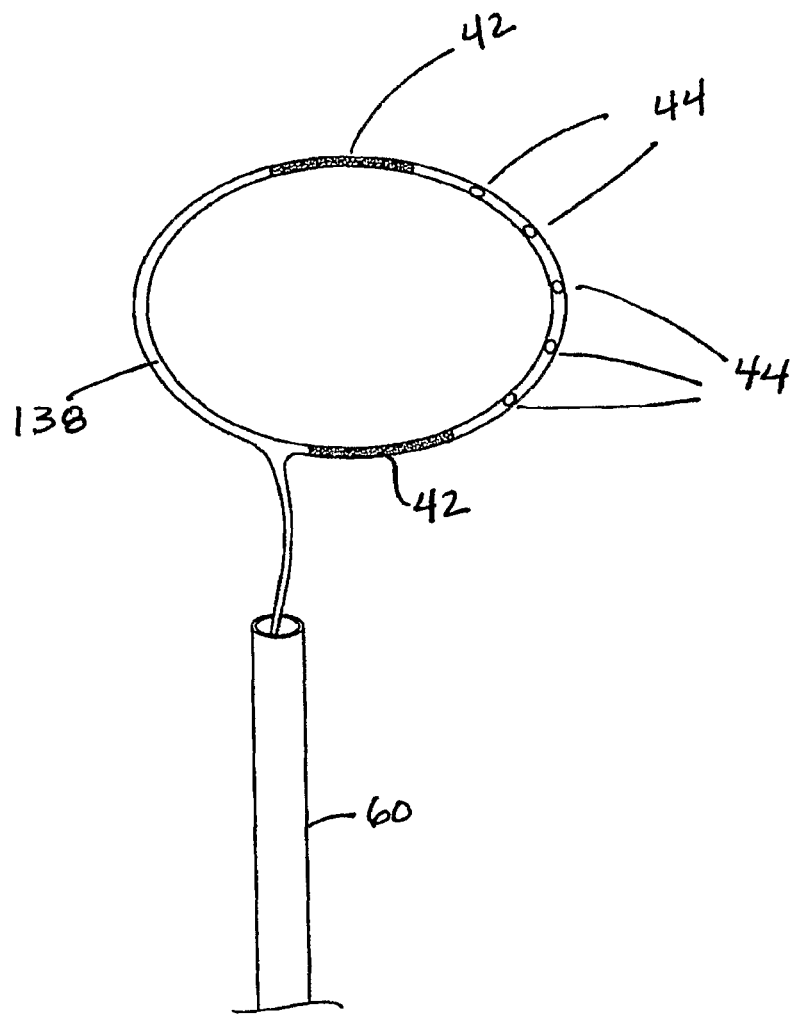
FIG. 17 illustrates another housing embodiment adapted for implantation in the pericardial space.

FIG. 17 illustrates another alternative embodiment of an ICD adapted for implantation within the pericardium. The housing 138 may also be configured as illustrated and described with regard to FIG. 9 where appropriate. In this embodiment, the second housing 138 is a continuous hoop sized to fit about a portion of the heart. The second housing contains one or more of electronic circuitry adapted to evaluate and initiate electrical cardiac therapy, a storage capacitor and an electrode structure comprising a sensing electrode, a pacing electrode and a therapy electrode. In the illustrated embodiment, the second housing 138 includes an electrode structure comprising a sensing electrode, a pacing electrode and a therapy electrode. The second implantable housing 138 is adapted and configured to lie within the pericardial space and at least partially conform to the shape of the ventricular portion of the heart.

Figure 22:
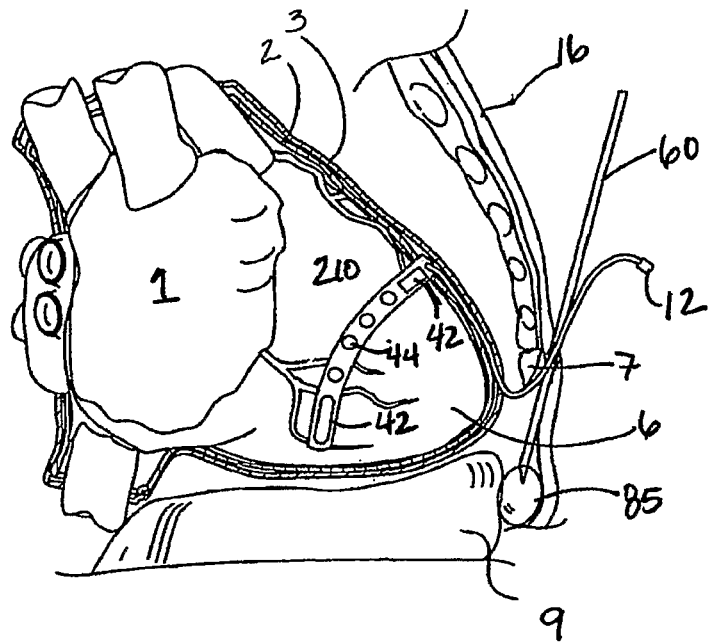
FIG. 22 illustrates a housing implanted into the pericardial space with a lead ready to be attached and a dissecting balloon creating a space for implantation.
Figure 23:
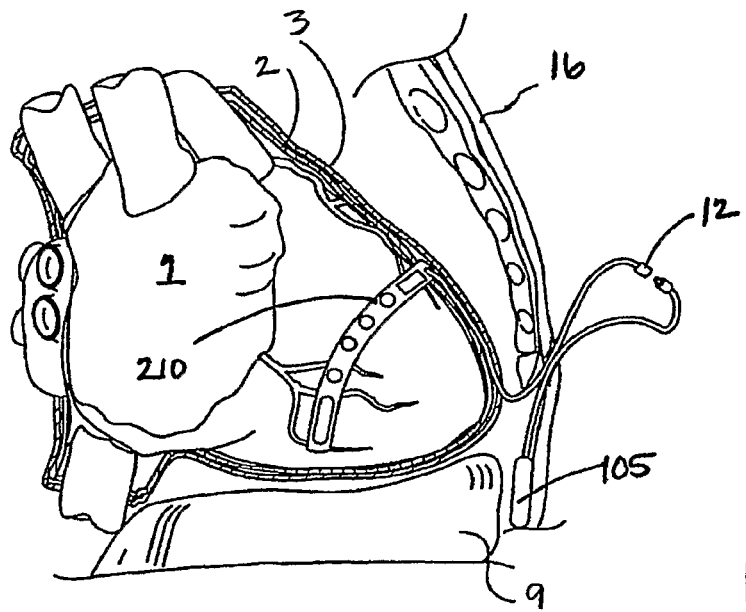
FIG. 23 illustrates a first housing implanted into the subcutaneous space and the connection of that housing to the housing in the pericardial space.

Similar to second housing 135, the second housing 138 has a stowed condition for delivery to an implantation location and a deployed condition for operation in an implantation location. The second housing 138 may also be maneuvered while in a stowed condition within the delivery tool 60 as shown in FIG. 8. During implantation, the delivery device 60 is maneuvered towards the apex 6 of the heart using any suitable surgical approach. One approach is illustrated in FIG. 10. There after, the second housing 138 is maneuvered into a deployed configuration with removing it from the sheath. The second housing 138 is placed so that when maneuvered into the deployed condition it is in proximity to the apex 6 of the heart 1. From the apex 6, the second housing 138 is advanced towards the ventricular/atrial groove for placement in a desired location on the surface of the epicardium 2. The battery supply may be implanted into the subcutaneous tissue as shown in FIGS. 22 and 23 and connected to the housing suitable connectors.

The housings described herein may include bands, arms, sections or portions of different geometry or lengths. Alternatively, the bands, arms, sections or portions of the housings are sufficiently long to encircle the heart remain in place by matching the diameter of a hoop, a hoop formed by the sections or the length of the second housing to match or nearly match the circumference of the desired placement on the heart. The circumference of the heart varies during the cardiac cycle. In any of the above embodiments, the second housing may be formed from a material that is flexible enough to deform with the movement of the heart while not unnecessarily constrict the heart or interfering with proper cardiac function. Optionally, a flexible portion, section or component may be built into or added onto the second housing to provide flexibility to compensate for the size variation of the heart.

Figure 18:
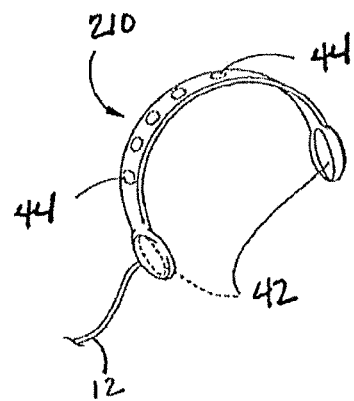
FIG. 18 illustrates another housing embodiment adapted for implantation in the pericardial space.

Other embodiments of the ICD components of the present invention may be positioned within the pericardial space on one side of the heart or only partially encircling the heart. FIG. 18 illustrates an embodiment of a "c" or "u" shaped second housing 210. This embodiment may have the advantage of simpler implantation since only one side of the heart is accessed. The shape of the housing 210 may be used to contour along an anterior surface, a posterior surface, a medial surface or a lateral surface of the epicardial layer of the heart between the apex and the pulmonary veins. The second housing 210 contains at least one of, two of or all of: electronic circuitry adapted to evaluate and initiate electrical cardiac therapy, a storage capacitor and an electrode structure comprising a sensing electrode, a pacing electrode and a therapy electrode. In the illustrated embodiment, the second housing 210 contains an electrode structure. In the illustrated embodiment, the therapy electrodes are positioned in the distal ends of the device. Other electrode positions are possible. For example, the therapy electrodes may be placed along the length or in a combination of locations including the ends and along the length along with the pacing and sensing electrodes. The remainder of the housing 210 may be used to for the electronics (either or both of the power storage 114 and circuitry 112) and/or the battery. When in position on the heart, the therapy electrodes may be both on a portion of the anterior portion of the heart, both on a posterior portion of the heart, or where electrodes are placed on both the anterior portion and the posterior portion of the heart.

Figure 19:
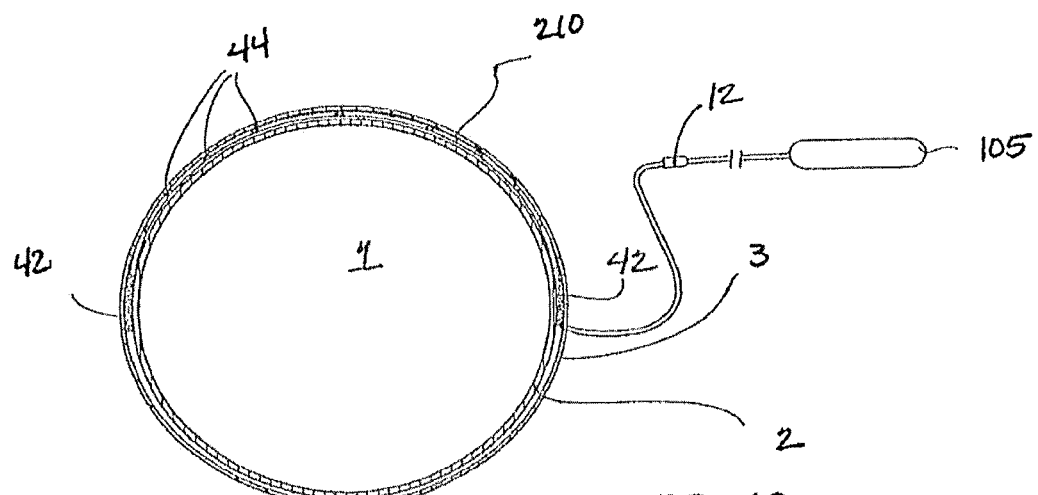
FIG. 19 is a schematic section view of the housing of FIG. 18 within the pericardial space.
Figure 20:
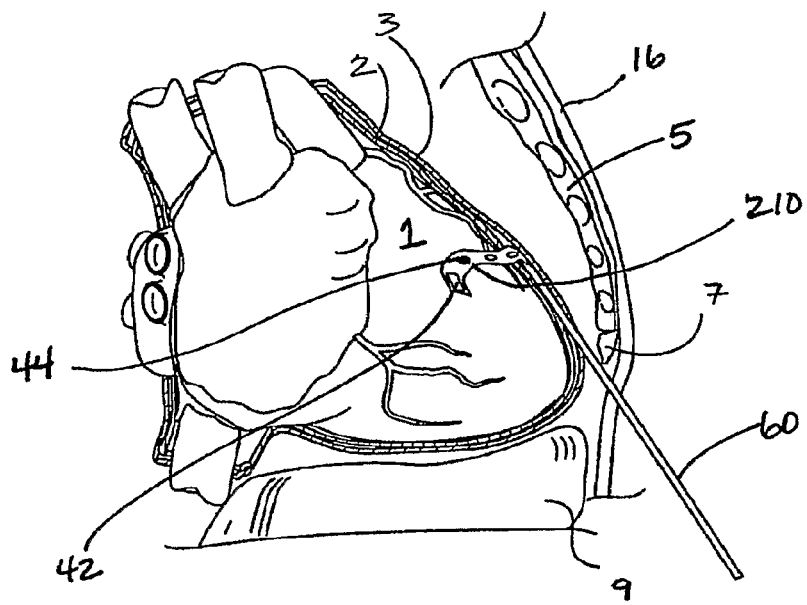
FIG. 20 illustrates a method of implanting a housing into the pericardial space using a sub-xiphoid approach.
Figure 21:
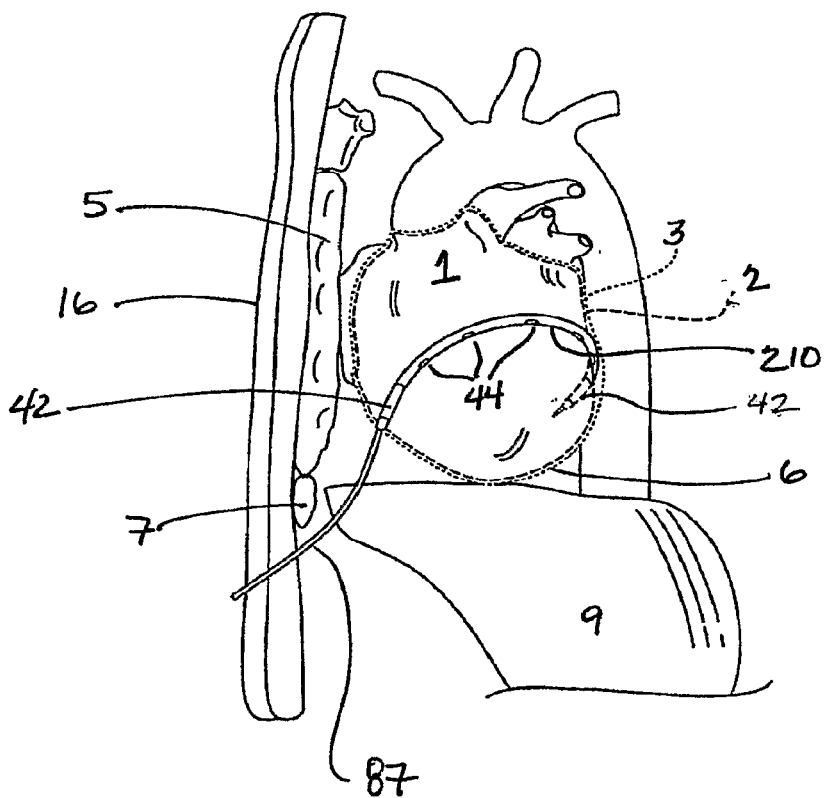
FIG. 21 illustrates the use of a curved or shaped stylet to implant a housing within the pericardial space.
Figure 24:
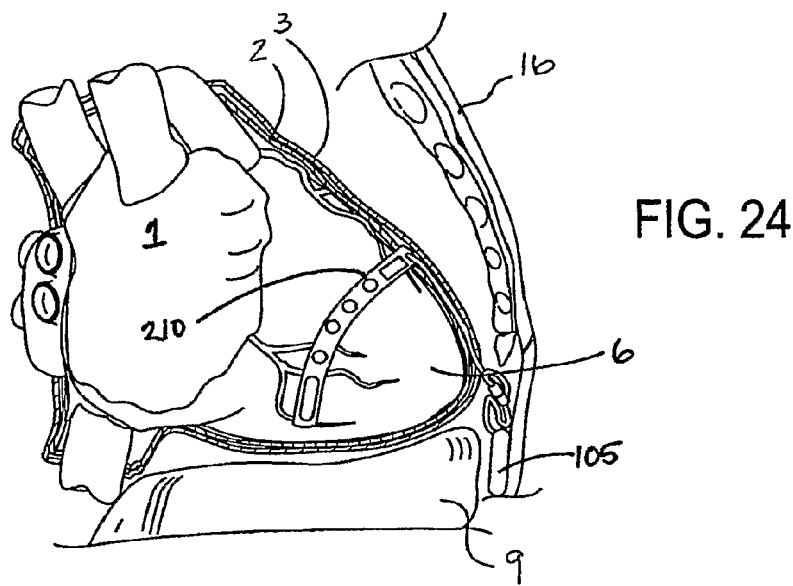
FIG. 24 illustrates a housing implanted into the pericardial space.

FIG. 19 illustrates a schematic of an embodiment of second housing 210 in FIG. 18 implanted within the pericardial space 3 of the heart 1. The second housing 210 is also shown connected to a first housing 105 using suitable connectors 12. The housing 105 contains a battery suited for use in an ICD system. One method of implanting the housing 210 begins with a sub-xiphoid process approach using an appropriate delivery device 60 as illustrated in FIG. 10. As shown in FIG. 20, the second housing 210 is introduced into and across the pericardial space 4. Optionally, as shown in FIG. 21, a stylet or other semi-rigid or shaped guide device to be attached to the housing 210 or placed within a lumen 256 in all or part of the housing (see, e.g., FIGS. 25, 25A and 25B). The flexible housing 210 is then made rigid or contoured into a desired shape induced by the guide device. The new semi-rigid or rigid device is advanced about the pericardial space into the desired position to apply therapy to the heart as illustrated in FIG. 21. As shown in FIG. 22, the second housing 210 is fully deployed within the pericardium and connector 12 is ready to be connected to another ICD component. FIG. 22 also illustrates using a balloon dissector 85 to form a cavity for a battery housing implantation site in the abdominal cavity or other easy to reach implant location to ease the burden of battery replacement. In FIG. 23 the housing 210 is connected to a battery within the implantable housing 105. FIG. 24 illustrates the implanted ICD components.

Any of the second housing embodiments described herein may be modified to include anchoring means for securing the housing to the epicardium or within the pericardial space. Anchoring means includes using conventional anchoring techniques such as adhesives, hooks, barbs or other mechanical fixation techniques suited for securing devices to the epicardium or within the pericardial space.

Figure 25:
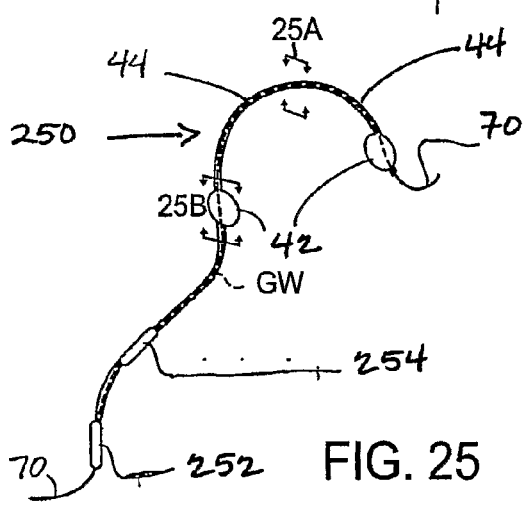
FIG. 25 illustrates an isometric view of a ICD have a guide wire lumen.
Figure 25A:
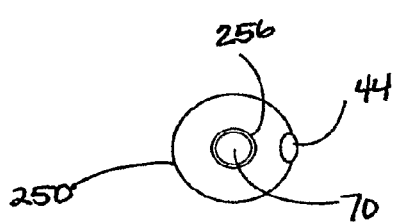
FIG. 25A illustrates the section view 25A in FIG. 25.
Figure 25B:
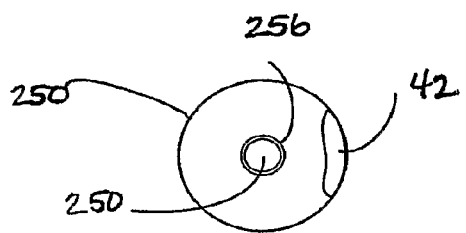
FIG. 25B illustrates the section view 25B in FIG. 25.

As illustrated above with regard to FIGS. 12-16, pericardial space implant procedures may be furthered through the use a guide wire 60 or stylet. All or a few of the ICD components of the present invention may be adapted to include a guide wire lumen or other feature to accommodate the use of a guide wire for component implantation. In the embodiment illustrated in FIG. 25, a second housing 250 has been modified to include a lumen 256 suitable for use with a guiding structure such as a guide wire or a stylet. In this embodiment, the housing 250 includes all the components of an ICD system including a battery 252, electronics 254 and an electrode component 70 having sensing and pacing electrodes 44 and therapy electrodes 42. FIG. 25A illustrates a portion of the housing 250 where the sensing electrode is positioned within the sidewall. FIG. 25 B illustrates the portion of the housing 250 containing the therapy electrode 42 within the sidewall. FIGS. 25, 25A and 25B. Here, housing 250 is a flexible tube with an elongate, generally cylindrical body. The housing 250 also includes integrally formed ICD components. While illustrated with a cylindrical shape, the housing 250 could have any of a number of cross-sectional shapes such as rectangular, oval, elliptical, crescent, polygonal or others.

Alternative ICD components may be adapted for delivery to an implantation location using a hollowed cannula or other suitable delivery device while in the stowed condition. These alternatives include designs with a number of different geometries as well as including stowed and deployed configurations that enable minimally invasive implantation techniques to be utilized.

Figures 26A, 26B, 27A, 27B:
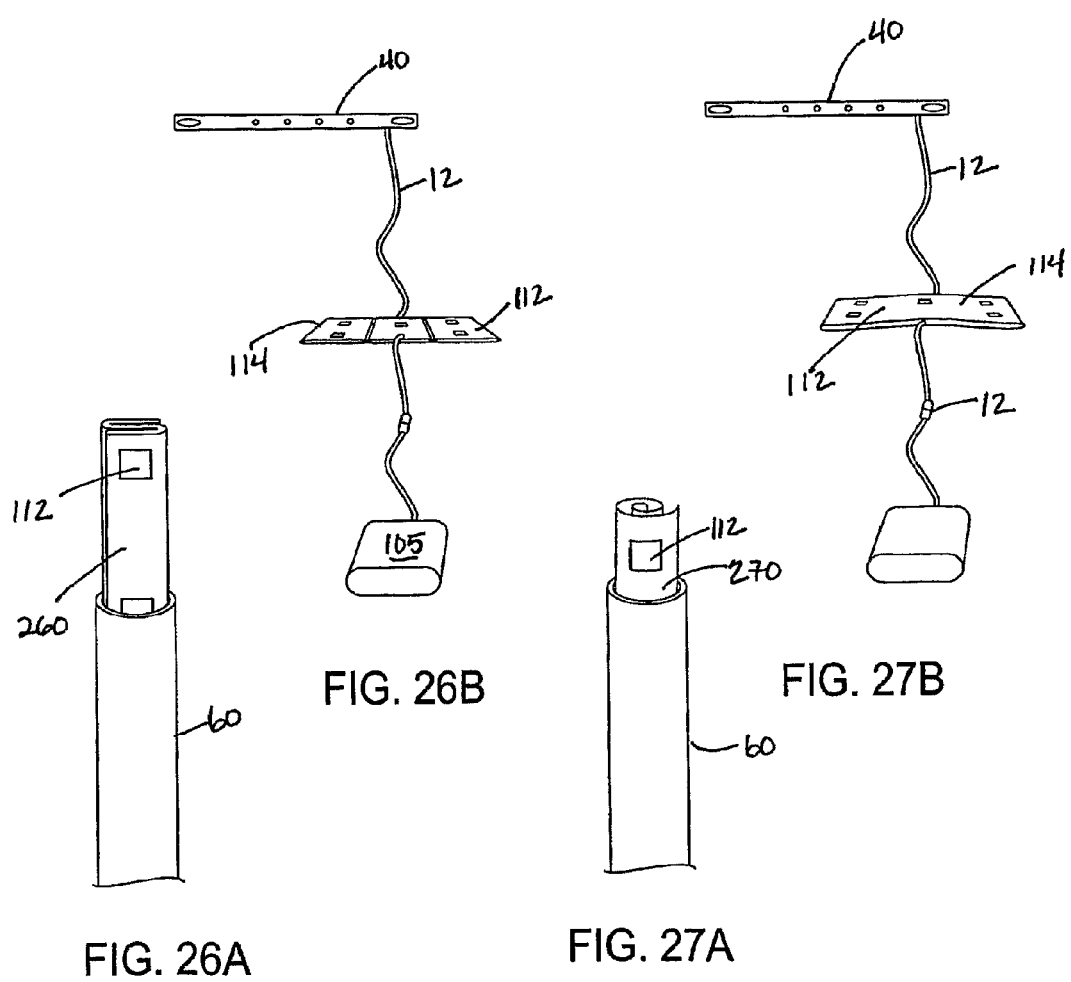
FIGS. 26A and 26B illustrate a folded housing in a stowed and deployed condition, respectively.
FIGS. 27A and 27B illustrate a rolled housing in a stowed and deployed condition, respectively.

One stowed ICD embodiment is illustrated in FIGS. 26A and 26B. In this embodiment, the ICD components are folded into a stowed condition for insertion into the body and movement to the implant site. As illustrated in FIG. 26A, the housing 260 is folded into a stowed configuration suited for delivery using the delivery device 60. The housing 260 may be inserted into the body using the techniques described and illustrated in FIG. 31 with or without the aid of stylet 87, 89. Once in the desired implant site, the folded housing is unfolded as shown in FIG. 26B and connected to other ICD components into an operational configuration. The folded ICD may contain all or part of the components needed to form an ICD. In the illustrated embodiment, the folded housing 260 includes electronic circuitry 112 adapted to evaluate and initiate electrical cardiac therapy and a storage capacitor 114. Multiple folded or stowed ICD components may be used to decrease the size of openings needed for implantation. After implantation and deployment, the individual ICD components may be connected using conventional tunneling techniques and suitable biocompatible electrical connectors as shown in FIG. 26B.

Figure 28:
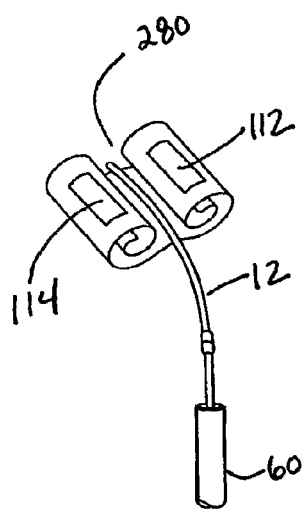
FIG. 28 illustrates another rolled housing embodiment in a stowed condition.

FIGS. 27A and 27B illustrate second housing embodiment adapted for delivery to an implantation location using a hollowed cannula or suitable delivery tool while in the stowed condition. As illustrated in FIG. 27A, the stowed condition for housing 270 is rolled. In this embodiment, the housing 270 is rolled from one side into a generally cylindrical shape like a scroll. The housing 270 may be inserted into the body using the techniques described and illustrated in FIG. 31 with or without the aid of stylet 87, 89. After insertion into the body and movement to the desired location, the housing 270 unrolls from the stowed condition into the deployed condition as shown in FIG. 27B. The deployed condition is unrolled as shown. FIG. 28 illustrates an alternative rolled housing 280 where two sides of the housing are rolled towards the center while in the stowed condition. In the deployed condition, the two sides are unrolled and appear ready for operation as illustrated in FIG. 27B.

Figure 29:
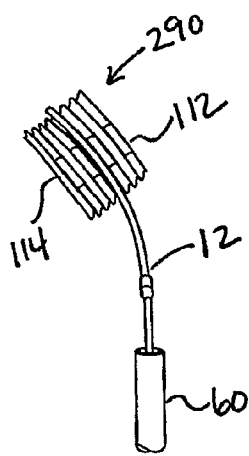
FIGS. 29 and 30 illustrate an expandable or inflatable housing in a stowed (uninflated or unexpanded) condition and a deployed (inflated or expanded) condition, respectively.
Figure 30:
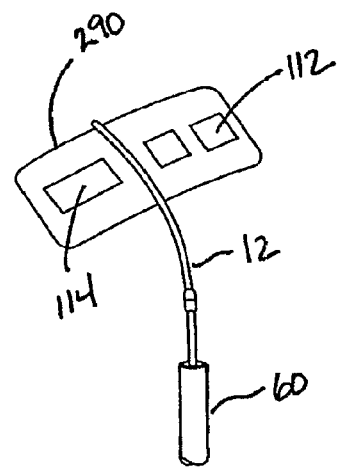

FIGS. 29 and 30 illustrate another embodiment of a compact, deployable ICD component that, while in the stowed condition, is adapted for delivery to an implantation location using a hollowed cannula or other suitable delivery device. In the illustrated embodiment, the housing 290 has a stowed condition that is uninflated (FIG. 29) and a deployed condition that is inflated (FIG. 30). The housing 290 includes one or more or all ICD components formed on a bellows or balloon or other expandable inflatable structure. After insertion and positioning, the bellows are expanded into the deployed condition shown in FIG. 30. In one embodiment, an implantation pocket or space has been created prior to the insertion of the device as described herein with regard to FIGS. 22, 31, 32, 33 or using the techniques in FIGS. 34A and 34B. In another embodiment, the expansion of the housing 290 is used to create a pocket used for the implant site. In this way, a cavity may be formed using the second housing to create an implantation site. Additionally, the movement of the second housing from a stowed condition to a deployed condition may be used to form a cavity within the body used for an implantation site.

Figure 31:
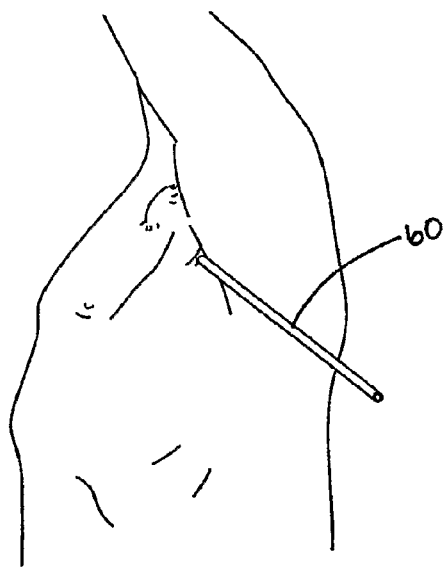
FIGS. 31-33 illustrate alternative minimally invasive implantation approaches.

FIG. 31 illustrates the use of hollow cannula, needle or other suitable device to access insertion points or implantation site access points that may be readily hidden. In the illustrated embodiment of FIG. 31, the access point is under the arm. Other alternative points include underneath the breast or other such areas where a small insertion point for implantation site access may be used.

Figure 32:
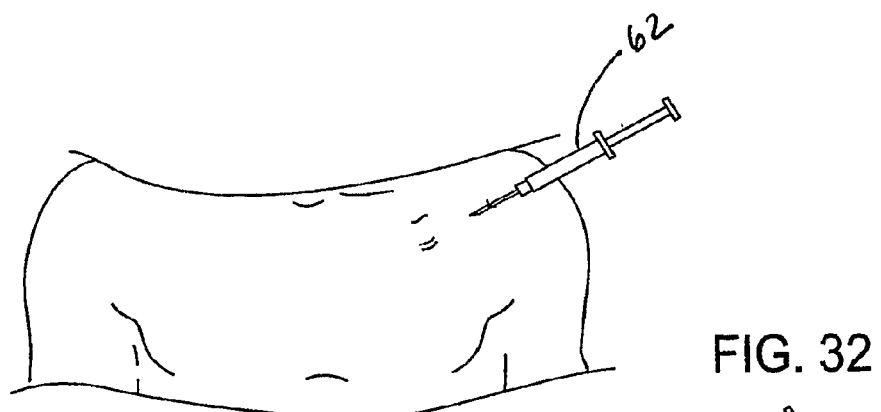
Figure 33:
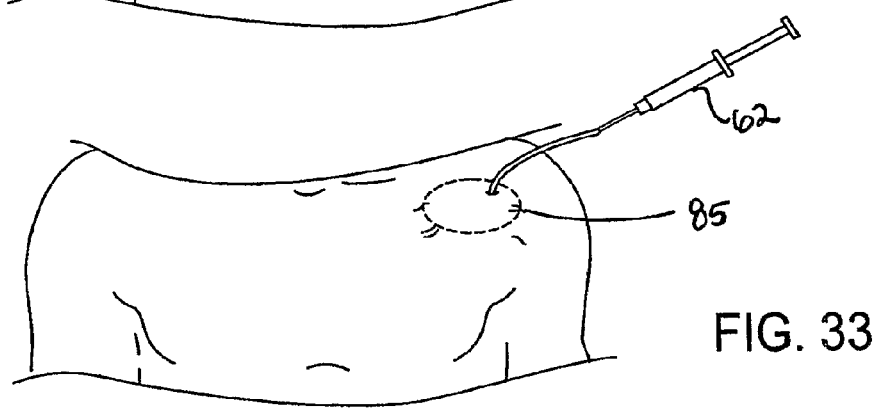
Figure 34A:
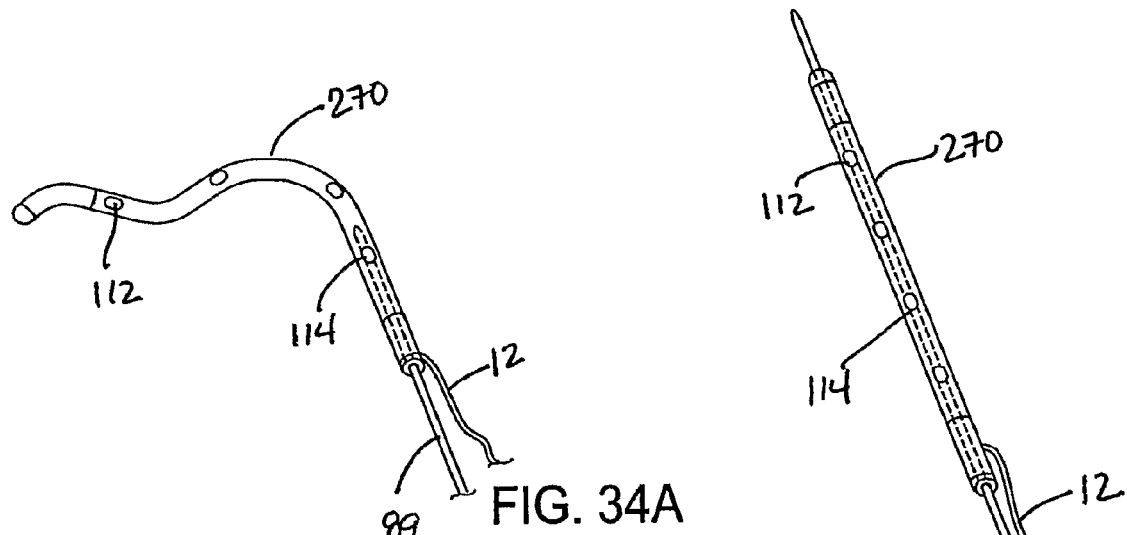
FIGS. 34A and 34B illustrate the use of a stylet for making a flexible housing rigid or semi-rigid during implantation.
Figure 34B:
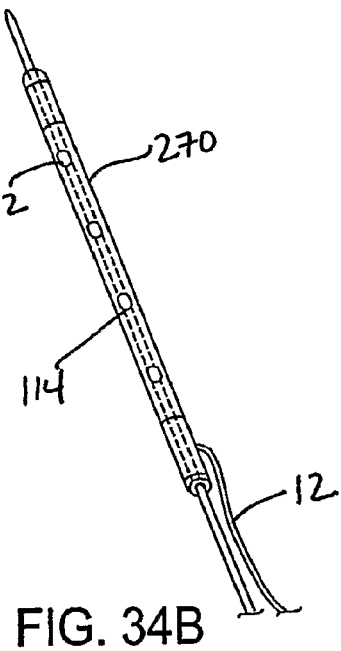

An exemplary minimally invasive implantation technique is illustrated FIGS. 32 and 33. A shown in FIG. 32, a needle is injected into the subcutaneous space. Next, as shown in FIG. 33 a balloon dilator is inserted through the needle. Thereafter, the balloon is inflated or expanded to create a space within the subcutaneous space. The cavity or pocket is being created in the skin by using the balloon dissector to separate the various tissue layers. After the subcutaneous space has been created, one or more of the components described herein is inserted into the space. Housings that may be stowed such as rolled, folded, collapsed or otherwise stowed may then be inserted into the created space in a stowed or collapsed condition. Once within the created space, the stowed component may be moved into a desired implantation location and then converted to a deployed condition. Alternatively, a component may be placed in the created space in a condition that is ready for operation (i.e., does not involve movement from a stowed to deployed configuration).

The minimally invasive incisions are illustrated in the embodiments of FIGS. 22 and 23. In these illustrations, minimally invasive techniques are used to create a space within the subcutaneous space for implantation of a first implantable housing containing a battery. It is to be appreciated that the stylet 89 illustrated in FIGS. 34A and 34B may provide access to numerous subcutaneous implant sites. Additionally, the stylets 89, 87 may be used to implant long cylindrical components, among other, such as the cylindrical battery and/or circuitry illustrated in FIGS. 37 and 38.

It is to be appreciated that other techniques used during cosmetic surgery to create small openings or incisions or the use of small injection holes to create access for tools could also be applied here. The tools are then used to create an implantation space. Next, compacted or stowed components are inserted into the cavity through the small hole and deployed as described herein.

FIG. 35 illustrates another embodiment of a second housing 290 containing electronic circuitry 112 and a capacitor 114 are used in conjunction with a first housing 105 containing a battery. The second housing 290 is connected to a conventional electrode structure 40 (not shown). The stylet technique illustrated in FIGS. 34A and 35 and may allow the housing 290 to be placed deeper into the tissue as measured from the incision. A deeper implantation site for the second housing 290 then allows the first housing 105 for the battery to remain closer to implant site for easy access when battery replacement is needed. FIG. 36 illustrates a battery housing 105 in the first implantation site that is closer to the surface of the skin than the second implantation where the housing 260 is implanted. In this embodiment the battery housing 260 may be implanted closer to the surface of the skin and the capacitor and electronic circuitry placed on housing 260) may be implanted at a deeper location within the tissue.

Figure 38:
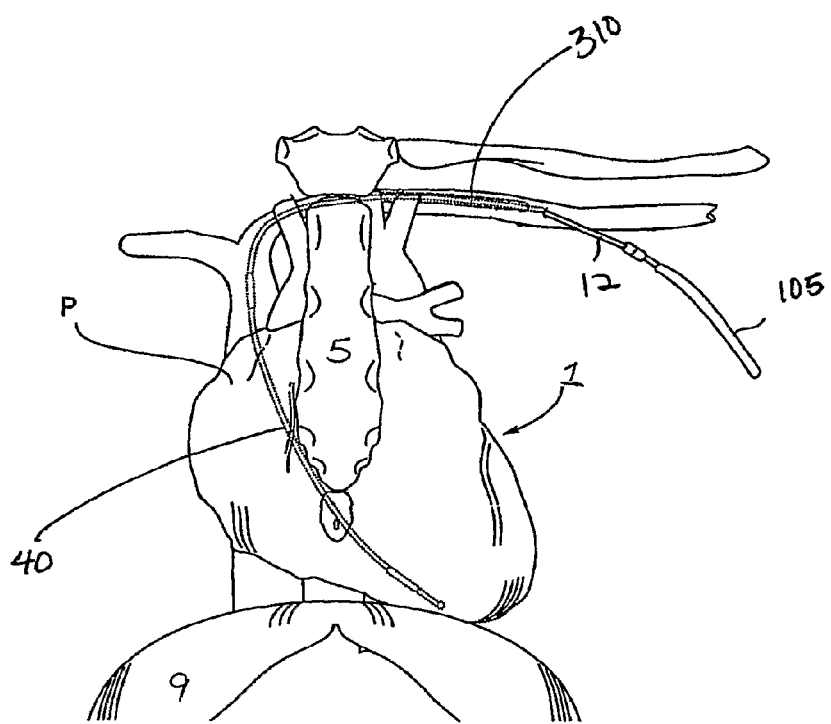
FIG. 38 illustrates a first and second housing embodiments in the form of elongate cylinders where the first housing is adapted for subcutaneous implantation and the second housing is adapted for implantation into the vasculature.

FIGS. 37 and 38 also illustrate embodiments of the second implantable housing formed from an elongate, generally cylindrical body. These embodiments of the second housing are adapted for delivery to an implantation location using a hollowed cannula or other suitable delivery device 60. In the embodiment of FIG. 37, the second implantable housing 310 is adapted for subcutaneous implantation. The housing 310 is attached to a conventional electrode structure 40 and an elongate cylindrical first housing 105 containing a battery. The second housing 310 contains one or both of the electronic circuitry or capacitors needed for ICD operation. Two housings 310 could be used where one contains the circuitry and the other contains the capacitor. As illustrated in FIG. 37, a conventional electrode lead within the vasculature is attached to an embodiment of the elongated cylindrical electronics package 310. The elongated cylindrical electronic circuitry package 310 is connected using suitable connectors to an elongated cylindrical battery 105. In this illustrative embodiment, both the electronic circuitry package and the battery are outside of the vasculature. As illustrated in FIG. 38, a conventional electrode lead 40 within the vasculature is attached to an embodiment of the elongated cylindrical electronic circuitry package 310 that is adapted for implantation within the vasculature. The elongated cylindrical electronic circuitry package 310 is connected using suitable connectors 12 that exit the vasculature and are connected to an elongated cylindrical battery 105. It is to be appreciated that battery housing 105 may have a different shape and/or size than the illustrated elongated cylinder.

It is to be appreciated that the housings illustrated and described in FIGS. 26A-30, 37 and 38 could be used in any combination with the implantable housing embodiments described above containing electrode structures. For example, the housing 210 having an electrode structure that is adapted for implantation into the pericardial space 4 could be used in an ICD system where the electronic circuitry 112 and capacitor 114 is provided by a housing described in any of FIGS. 26A to 30. In this way, ICD components provided in implantable housings adapted for implantation within the pericardial space may be combined with ICD components provided in implantable housings adapted for implantation in the vasculature or subcutaneously.

In another embodiment, there is provided an implantable medical device for delivering electrical cardiac therapy having one or more implantable structures containing the following electrically connected components: a battery, electronic circuitry adapted to evaluate and initiate electrical cardiac therapy, a storage capacitor and an electrode structure comprising a sensing electrode, a pacing electrode and a therapy electrode. The one or more implantable structures are adapted and configured for implantation within the pericardial space. In one embodiment, at least a portion of the implantable structure is in direct contact with the epicardium. In other alternative embodiments, the implantable housings described and illustrated with regard to FIGS. 5, 7, 9, 11, 16, 17, 18, 21, 22, and 25 are modified to contain all ICD components within, on or about a single implantable housing adapted for implantation within the pericardium. In other alternative embodiments, the implantable housings described and illustrated with regard to FIGS. 5, 7, 9, 11, 16, 17, 18, 21, 22, and 25 are modified to contain all ICD components, in various combinations on two or more implantable housings adapted for implantation within the pericardium.

Apparatuses and methods are disclosed relating to various types of implantable ICDs or ICD components with geometries, shapes and sizes adapted for implantation subcutaneously, within the vasculature or within the pericardial space. In one application, for example, some embodiments are placed completely in the subcutaneous, submuscular or pericardial space without the need to place leads or electrodes in the vasculature of the patient. One set of embodiments of the invention provides a variety of configurations for delivering cardioversion/defibrillation therapy with a vector of energy controlled by electronic circuitry 112/114. In one form of the invention, the implantable housing can be conveniently implanted in a surgically-created subcutaneous or submuscular pocket formed over or near a portion of the cardiac notch, or sternum of a patient and adjacent to a portion of pectoralis major.

In one embodiment, the ICD components described herein are electrically coupled to one or more elongated, coil-type high voltage electrodes with the electrodes disposed in a location providing defibrillation vectors covering adequate mass of myocardial tissue to achieve defibrillation and deliver pacing therapy. Specifically, leads may be substantially implanted within the pericardial space.

Some ICD components described herein may be constructed of stainless steel, titanium or ceramic as described in U.S. Pat. Nos. 4,180,078 "Lead Connector for a Body Implantable Stimulator" to Anderson and 5,470,345 "Implantable Medical Device with Multi-layered Ceramic Enclosure" to Hassler, et al. The electronic components 112, 114 may be incorporated as appropriate on a polyamide flex circuit, printed circuit board (PCB) or ceramic substrate with integrated circuits packaged in leadless chip carriers and/or chip scale packaging (CSP).

The electronic circuitry adapted to evaluate and initiate electrical cardiac therapy can take any of the known forms that detect a tachyarrhythmia from the sensed electrogram (EGM) and provide cardioversion/defibrillation shocks as well as post-shock pacing as needed. The circuitry is adapted to function employing the first and second and, optionally, the third cardioversion-defibrillation electrodes as well as the EGM sensing and pacing electrodes.

ICD functions are controlled by means of stored software, firmware and hardware that cooperatively monitor the EGM, determine when a cardioversion-defibrillation shock or pacing is necessary, and deliver prescribed cardioversion-defibrillation and pacing therapies. Suitable control circuitry is set forth in U.S. Pat. Nos. 5,163,427 "Apparatus for Delivering Single and Multiple Cardioversion and Defibrillation Pulses" to Keimel; 5,188,105 "Apparatus and Method for Treating a Tachyarrhythmia" to Keimel and 5,314,451 "Replaceable Battery for Implantable Medical Device" to Mulier for selectively delivering single phase, simultaneous biphasic and sequential biphasic cardioversion-defibrillation shocks.

Sensing and pacing electrodes may be operated in the manner disclosed in U.S. Pat. No. 5,331,966 "Subcutaneous Multi-Electrode Sensing System, Method and Pacer" to Bennett, et al.

Certain steps in the performance of the detection algorithm criteria are cooperatively performed in a microcomputer, including microprocessor, RAM and ROM, associated circuitry, and stored detection criteria that may be programmed into RAM via a telemetry interface conventional in the art. Data and commands may be exchanged between microcomputer and timing and control circuits, pacer timing/amplifier circuits, and high voltage output circuits via a suitable bidirectional data/control bus. The algorithms and functions of the microcomputer and timer and control circuits employed and performed in detection of tachyarrhythmias are set forth, for example, in U.S. Pat. Nos. 5,991,656 "Prioritized Rule Based Apparatus for Diagnosis and Treatment of Arrhythmias" to Olson, et al and 5,193,535 "Method and Apparatus for Discrimination of Ventricular Tachycardia from Ventricular Fibrillation and for Treatment Thereof" to Bardy, et al, for example. Particular algorithms for detection of ventricular fibrillation and malignant ventricular tachycardias can be selected from among the comprehensive algorithms for distinguishing atrial and ventricular tachyarrhythmias from one another and from high rate sinus rhythms that are set forth in the '656 and '535 patents.

The detection algorithms are also sensitive and specific for the presence or absence of life threatening ventricular arrhythmias, e.g., ventricular tachycardia (V-TACH) and ventricular fibrillation (V-FIB). Additionally, the operational circuitry can detect the presence of atrial fibrillation (A FIB) as described in Olson, W. et al. "Onset And Stability For Ventricular Tachyarrhythmia Detection in an Implantable Cardioverter and Defibrillator," Computers in Cardiology (1986) pp. 167-170. Detection can be provided via R-R Cycle length instability detection algorithms. Once A-FIB has been detected, the operational circuitry will then provide QRS synchronized atrial cardioversion/defibrillation using the same shock energy and wave shapes used for ventricular cardioversion/defibrillation.

Operating modes and parameters of the detection algorithm are programmable and the algorithm is focused on the detection of V-FIB and high rate V-TACH (>240 bpm).

Additional details regarding ICD components and operation may be found in US Patent Application Publication 2006/0247688 to Olson, et, al; US Patent Application Publication 2004/0068302 to Rodgers, et, al; and US Patent Application Publication 2002/0035380 to Rissmann, et, al. each of these and all other patents, published patent applications, and publications mentioned in this application are incorporated herein by reference in its entirety.

It will be apparent from the foregoing that while particular embodiments of the invention have been illustrated and described, various modifications can be made without departing from the spirit and scope of the invention. For example, in one or more alternative embodiments, the housing 105 illustrated in FIGS. 11, 16, 19, 23 and 24 may not contain the battery used in the operation of the ICD. Instead, the housing 105 contains other ICD component(s) not already provided. In these alternative embodiments, the battery is provided in locations such as those illustrated and described in FIGS. 35, 36, 37 and 38 using the techniques described and illustrated in FIGS. 31, 32, 33, 34A, 34B and 21.

Accordingly, it is not intended that the invention be limited, except as by the appended claims.

What is claimed is:

1. An implantable medical device for delivering electrical cardiac therapy, comprising:
a first implantable housing containing a battery;
a second implantable housing separate from the first implantable housing and containing electronic circuitry adapted to evaluate and initiate electrical cardiac therapy, the electronic circuitry including at least one control circuit, and at least one of: a storage capacitor and an electrode structure comprising a sensing electrode, a pacing electrode and a therapy electrode, wherein the electronic circuitry, the storage capacitor or the electrode structure is electrically connected to the battery; and wherein the second implantable housing has a predefined curve that complies with one or more portions of the contours of a human heart, wherein the second implantable housing is flexible and configured to deform with the movement of the heart while not interfering with proper heart function, and wherein the second implantable housing is adapted and configured to lie within the pericardial space of the human heart, and wherein the second housing has a stowed condition for delivery to an implantation location and a deployed condition for operation in an implantation location.

2. The implantable medical device for delivering electrical cardiac therapy according to claim 1 wherein the second implantable housing contains a storage capacitor and an electrode structure comprising a sensing electrode, a pacing electrode and a therapy electrode.

3. The implantable medical device for delivering electrical cardiac therapy according to claim 1 wherein the second implantable housing is a flexible band.

4. The implantable medical device for delivering electrical cardiac therapy according to claim 1 wherein the second implantable housing is sufficiently long to encircle a portion of the ventricular portion of the heart.

5. The implantable medical device for delivering electrical cardiac therapy according to claim 1 wherein the stowed condition is rolled and deployed condition is unrolled.

6. The implantable medical device for delivering electrical cardiac therapy according to claim 1 wherein the stowed condition is uninflated and the deployed condition is inflated.

7. The implantable medical device for delivering electrical cardiac therapy according to claim 1 wherein the deployed condition includes a first section adapted to conform to a portion of the posterior ventricular epicardial portion of the heart and a second section adapted to conform to a portion of the anterior ventricular epicardial portion of the heart.

8. The implantable medical device for delivering electrical cardiac therapy according to claim 7 wherein the first section is magnetically attached to the second section when the second housing is in a deployed condition.

9. The implantable medical device for delivering electrical cardiac therapy according to claim 1 wherein the second implantable housing comprises a predefined curve in a deployed configuration configured to comply with one or more outer portions of the contours of a heart.

10. The implantable medical device for delivering electrical cardiac therapy according to claim 1 wherein the second implantable housing in configured to completely encircle an outer portion of a heart in a deployed configuration.

11. The implantable medical device for delivering electrical cardiac therapy according to claim 1 wherein the second implantable housing is configured to partially encircle an outer portion of a heart in a deployed configuration.

* * * * *